US010379873B2

(12) United States Patent
Leon et al.

(10) Patent No.: US 10,379,873 B2
(45) Date of Patent: Aug. 13, 2019

(54) DISTRIBUTED PROCESSING SYSTEM

(71) Applicant: TYCO FIRE & SECURITY GMBH, Neuhausen am Rheinfall (CH)

(72) Inventors: Gustavo Leon, Tamarac, FL (US); Stewart E. Hall, Wellington, FL (US); Craig Trivelpiece, Las Vegas, NV (US); Paul B. Rasband, Lantana, FL (US)

(73) Assignee: Tyco Fire & Security GmbH, Neuhausen am Rheinfall (CH)

(*) Notice: Subject to any disclaimer, the term of this patent is extended or adjusted under 35 U.S.C. 154(b) by 0 days.

(21) Appl. No.: 14/464,091

(22) Filed: Aug. 20, 2014

(65) Prior Publication Data
US 2015/0249588 A1 Sep. 3, 2015

Related U.S. Application Data

(60) Provisional application No. 61/973,962, filed on Apr. 2, 2014, provisional application No. 61/946,054, filed on Feb. 28, 2014.

(51) Int. Cl.
G06F 9/4401 (2018.01)
H04L 12/46 (2006.01)
(Continued)

(52) U.S. Cl.
CPC ............ G06F 9/4416 (2013.01); A61B 17/00 (2013.01); G01S 5/02 (2013.01); G01S 5/0236 (2013.01);
(Continued)

(58) Field of Classification Search
CPC ..... H04L 67/10; H04L 45/74; H04L 12/4625; H04L 43/0876; H04L 43/10;
(Continued)

(56) References Cited

U.S. PATENT DOCUMENTS 5,414,812 A 5/1995 Filip et al.
6,012,150 A * 1/2000 Bartfai ............... G06F 11/2023
709/248
(Continued)

FOREIGN PATENT DOCUMENTS

CN 1217078 A 5/1999
CN 1672060 A 9/2005
(Continued)

OTHER PUBLICATIONS

International Search Report and Written Opinion, PCT/US15/17931.
(Continued)

Primary Examiner — Chris Parry
Assistant Examiner — Chouat Abderrahmen
(74) Attorney, Agent, or Firm — Foley & Lardner LLP

(57) ABSTRACT

Described is a system that includes a queue cluster including first network devices that cooperate to communicate with end nodes of a network and to store information from the end nodes in memory, a processing cluster comprising second network devices that cooperate to perform one or more tasks on the information from the queue cluster, and a database cluster including third network devices that cooperate to provide storage for use by the processing cluster, with the queue cluster, the processing cluster, and the database cluster being part of a local network that is connectable to an external network, the local network including a wireless mesh network and for the one or more tasks, a network device among the second network devices is selected as a leader responsible for task execution.

20 Claims, 8 Drawing Sheets

(51) Int. Cl.

| | | |
|---|---|---|
| H04L 12/64 | (2006.01) | |
| H04L 29/08 | (2006.01) | |
| H04L 29/12 | (2006.01) | |
| H04L 9/00 | (2006.01) | |
| H04N 5/76 | (2006.01) | |
| H04W 16/26 | (2009.01) | |
| G01S 5/02 | (2010.01) | |
| G01S 13/76 | (2006.01) | |
| G08B 25/00 | (2006.01) | |
| H04W 8/26 | (2009.01) | |
| G08B 29/18 | (2006.01) | |
| H04W 88/04 | (2009.01) | |
| A61B 17/00 | (2006.01) | |
| G01S 13/87 | (2006.01) | |
| G08B 13/196 | (2006.01) | |
| H04W 4/38 | (2018.01) | |
| H04W 92/02 | (2009.01) | |
| H04L 12/26 | (2006.01) | |
| H04W 84/18 | (2009.01) | |

(52) U.S. Cl.
CPC .......... *G01S 5/0284* (2013.01); *G01S 13/765* (2013.01); *G01S 13/876* (2013.01); *G08B 13/19634* (2013.01); *G08B 25/009* (2013.01); *G08B 29/181* (2013.01); *G08B 29/188* (2013.01); *H04L 9/004* (2013.01); *H04L 12/4625* (2013.01); *H04L 12/6418* (2013.01); *H04L 61/106* (2013.01); *H04L 67/104* (2013.01); *H04L 67/12* (2013.01); *H04L 67/34* (2013.01); *H04N 5/76* (2013.01); *H04W 8/26* (2013.01); *H04W 16/26* (2013.01); *H04W 88/04* (2013.01); *G08B 13/19608* (2013.01); *G08B 25/007* (2013.01); *H04L 43/0805* (2013.01); *H04L 61/6013* (2013.01); *H04L 61/6072* (2013.01); *H04L 67/1051* (2013.01); *H04L 67/1093* (2013.01); *H04W 4/38* (2018.02); *H04W 84/18* (2013.01); *H04W 92/02* (2013.01); *Y04S 40/168* (2013.01); *Y04S 40/18* (2018.05)

(58) Field of Classification Search
CPC ..... H04L 12/6418; H04L 49/10; H04L 12/00; H04L 12/10; H04L 12/12; H04L 12/2838; H04L 12/58; H04L 25/4902; H04L 41/0672; H04N 7/181; H04N 5/23241; H04N 5/76; H04N 7/18; H04N 19/0003; H04N 19/00206; H04N 19/00266; H04N 19/00733; H04N 5/147; H04N 5/77; H04N 5/772; H04N 5/775; H04N 5/781; H04N 5/9205; H04N 7/01
USPC .......... 340/572.1, 10.1, 568.1, 572.7, 572.8, 340/572.9, 506, 514, 577, 691.8, 572.4, 340/691.1, 10.3, 10.5, 571, 540, 572.3, 340/628, 10.2, 572.5, 815.45, 10.4, 5.7, 340/686.1, 505, 572.2, 815.4, 10.42, 501, 340/541, 568.5, 10.34, 10.51, 10.52, 10.6, 340/2.4, 539.11, 539.26, 539.27, 572.6; 709/206, 204, 208, 220, 224
See application file for complete search history.

(56) References Cited

U.S. PATENT DOCUMENTS

| | | |
|---|---|---|
| 6,208,247 B1 | 3/2001 | Loeffelholz et al. |
| 6,636,900 B2 * | 10/2003 | Abdelnur ............ H04L 29/06 709/203 |
| 6,873,260 B2 | 3/2005 | Lancos et al. |
| 6,888,459 B2 | 5/2005 | Stilp |
| 7,966,660 B2 | 6/2011 | Yermal et al. |
| 8,089,910 B2 | 1/2012 | Doh et al. |
| 8,260,893 B1 * | 9/2012 | Bandhole ............ G06F 9/5083 709/221 |
| 8,305,196 B2 | 11/2012 | Kennedy et al. |
| 8,331,544 B2 | 12/2012 | Kraus et al. |
| 8,477,687 B2 | 7/2013 | Iwasa |
| 8,572,290 B1 * | 10/2013 | Mukhopadhyay ........................ G06F 17/30094 709/251 |
| 8,572,600 B2 | 10/2013 | Chung et al. |
| 8,582,431 B2 | 11/2013 | Johansen |
| 8,848,721 B2 * | 9/2014 | Turunen ................. H04W 4/06 370/400 |
| 9,277,352 B1 * | 3/2016 | Ward ...................... H04L 67/02 |
| 2003/0097464 A1 * | 5/2003 | Martinez ................. H04L 29/06 709/238 |
| 2004/0090329 A1 | 5/2004 | Hitt |
| 2004/0109059 A1 | 6/2004 | Kawakita |
| 2005/0143133 A1 | 6/2005 | Bridgelall |
| 2006/0022816 A1 | 2/2006 | Yukawa |
| 2007/0073861 A1 | 3/2007 | Amanuddin et al. |
| 2007/0223451 A1 | 9/2007 | Ren et al. |
| 2007/0239350 A1 | 10/2007 | Zumsteg et al. |
| 2008/0068267 A1 | 3/2008 | Huseth |
| 2008/0136620 A1 | 6/2008 | Lee et al. |
| 2008/0291017 A1 | 11/2008 | Yermal et al. |
| 2009/0021634 A1 | 1/2009 | Chang |
| 2009/0222921 A1 | 9/2009 | Mukhopadhyay et al. |
| 2009/0322510 A1 * | 12/2009 | Berger ................... G06Q 10/08 340/539.1 |
| 2010/0226342 A1 | 9/2010 | Coiling et al. |
| 2011/0051656 A1 | 3/2011 | Hethuin et al. |
| 2011/0137614 A1 | 6/2011 | Wheeler et al. |
| 2011/0310779 A1 | 12/2011 | De Poorter et al. |
| 2011/0310791 A1 | 12/2011 | Prakash et al. |
| 2012/0310423 A1 | 12/2012 | Taft |
| 2013/0003645 A1 | 1/2013 | Shapira et al. |
| 2013/0064233 A1 | 3/2013 | Hethuin et al. |
| 2013/0239192 A1 | 9/2013 | Linga et al. |
| 2013/0317659 A1 | 11/2013 | Thomas et al. |
| 2014/0052832 A1 | 2/2014 | Dina et al. |
| 2014/0129135 A1 * | 5/2014 | Holden ................. G01C 21/30 701/420 |
| 2014/0222892 A1 * | 8/2014 | Lee ...................... G06F 21/6272 709/203 |
| 2015/0074178 A1 * | 3/2015 | Hong .................. H04L 67/1097 709/203 |
| 2015/0248299 A1 | 9/2015 | Rasband et al. |

FOREIGN PATENT DOCUMENTS

| | | |
|---|---|---|
| CN | 1871782 A | 11/2006 |
| CN | 101951341 A | 1/2011 |
| CN | 101364734 | 2/2011 |
| CN | 101976377 A | 2/2011 |
| WO | 0 814 393 | 12/1997 |
| WO | WO 01/06401 | 1/2001 |
| WO | WO 01/26329 | 12/2001 |
| WO | WO2004/068855 | 8/2004 |
| WO | WO 2013/159217 | 10/2013 |

OTHER PUBLICATIONS

International Search Report and Written Opinion, PCT/US15/17680.
International Search Report and Written Opinion, PCT/US15/17702.
International Supplementary Search Report, PCT/US2015/017931.
International Extended Search Report, PCT/US00/27515.
Asada, G. et al., "Wireless Integrated Network Sensors (Wins)" Proceedings of the Spie, Spie, Bellingham, VA, vol. 3673, Mar. 1, 1999, pp. 11-18.
Ying Zhou et al., *"Mobile Agent-based Policy Management for Wireless Sensor Networks,"*, Wireless Communications, Network-

(56) References Cited

OTHER PUBLICATIONS ing and Mobile Computing, 2005, Proceedings 2005 Int'l Conference on Wuhan, China, vol. 2, (Sep. 23, 2005), pp. 1207-1210.
European Search Report, PCT/US2015/017212.
Examination Report (China), May 2, 2018.
Office Action for U.S. Appl. No. 15/402,423, dated Jul. 26, 2018, 10 pages.
Chinese Office Action dated May 30, 2018 in corresponding application No. 201580016948.9.
Chen et al., Enix: a lightweight dynamic operating system for tightly constrained wireless sensor platforms, Proceedings of the 8th ACM Conference on Embedded Networked Sensor Systems, Nov. 3, 2010, http://sensys.acm.org/2010/Papers/p183-Chen.pdf.
Office Action for U.S. Appl. No. 14/463,738, dated Dec. 2, 2015, 7 pages.
Office Action tor U.S. Appl. No. 14/463,754, dated Jan. 11, 2018, 21 pages.
Office Action for U.S. Appl. No. 14/463,754, dated May 24, 2017, 21 pages.
Office Action for U.S. Appl. No. 14/463,754, dated Oct. 14, 2016, 17 pages.
Office Action for U.S. Appl. No. 14/463,830, dated Aug. 23, 2018, 20 pages.
Office Action for U.S. Appl. No. 14/463,830, dated Jun. 1, 2017, 14 pages.
Office Action for U.S. Appl. No. 14/463,830, dated Oct. 20, 2017, 19 pages.
Office Action for U.S. Appl. No. 14/463,830, dated Apr. 27, 2018, 21 pages.
Office Action for U.S. Appl. No. 14/464,070, dated Nov. 10, 2016, 14 pages.
Office Action for U.S. Appl. No. 14/603,602, dated Feb. 12, 2018, 22 pages.
Office Action for U.S. Appl. No. 14/603,602, dated May 31, 2017, 20 pages.
Office Action for U.S. Appl. No. 14/603,602, dated Oct. 7, 2016, 18 pages.
Office Action for U.S. Appl. No. 15/402,423, dated Apr. 20, 2018, 12 pages.
Office Action for U.S. Appl. No. 15/402,423, dated Sep. 22, 2017, 11 pages.
Office Action on U.S. Appl. No. 14/463,754 dated Jun. 14, 2018. 8 pages.
Office Action on U.S. Appl. No. 14/603,602 dated Jul. 3, 2018. 7 pages.
Office Action on U.S. Appl. No. 14/463,830 dated Apr. 27, 2018. 21 pages.

* cited by examiner

DISTRIBUTED PROCESSING SYSTEM

CLAIM OF PRIORITY

This application claims priority under 35 U.S.C. § 119(e) to provisional U.S. Patent Application 61/973,962, filed on Apr. 2, 2014, entitled: "Wireless Sensor Network", and provisional U.S. Patent Application 61/946,054, filed on Feb. 28, 2014, entitled: "Wireless Sensor Network", the entire contents of which are hereby incorporated by reference.

BACKGROUND

This specification relates generally to a distributed processing system.

Wireless sensor network/wireless device based data collection and control systems having remote server-based monitoring and report generation are used in applications such as home safety monitoring, electrical and water utility meter monitoring, and human and asset tracking. For example, it is common for businesses and homeowners to have a security system for detecting alarm conditions at their premises and for signaling conditions to a monitoring station or to authorized users of the security system.

SUMMARY

According to an aspect, a system includes a queue cluster including first network devices that cooperate to communicate with end nodes of a network and to store information from the end nodes in memory, a processing cluster comprising second network devices that cooperate to perform one or more tasks on the information from the queue cluster, and a database cluster comprising third network devices that cooperate to provide storage for use by the processing cluster, with the queue cluster, the processing cluster, and the database cluster being part of a local network that is connectable to an external network, the local network comprising a wireless mesh network and for the one or more tasks, a network device among the second network devices is selected as a leader responsible for task execution.

Any two or more of the features described in this specification, including this summary section, may be combined to form implementations not specifically described herein.

All or part of the foregoing may be implemented as a computer program product comprised of instructions that are tangibly stored on one or more non-transitory machine-readable storage media/hardware devices, and which are executable on one or more processing devices. All or part of the foregoing may be implemented as an apparatus, method, or network system that may include one or more processing devices and memory to store executable instructions to implement functionality.

The details of one or more examples are set forth in the accompanying drawings and the description below. Further features, aspects, and advantages will become apparent from the description, the drawings, and the claims.

DETAILED DESCRIPTION

Described herein are examples of network features that may be used in various contexts including, but not limited to, security/intrusion and alarm systems. Example security systems may include an intrusion detection panel that is electrically or wirelessly connected to a variety of sensors. Those sensors types may include motion detectors, cameras, and proximity sensors (used e.g., to determine whether a door or window has been opened) or whether a body has moved passed or within sensing range of the proximity sensor. Typically, such systems receive a relatively simple signal (electrically open or closed) from one or more of these sensors to indicate that a particular condition being monitored has changed or become unsecure.

For example, typical intrusion systems can be set-up to monitor entry doors in a building. When a door is secured, a proximity sensor senses a magnetic contact and produces an electrically closed circuit. When the door is opened, the proximity sensor opens the circuit, and sends a signal to the panel indicating that an alarm condition has occurred (e.g., an opened entry door).

Data collection systems are becoming more common in some applications, such as home safety monitoring. Data collection systems employ wireless sensor networks and wireless devices, and may include remote server-based monitoring and report generation. As described in more detail below, wireless sensor networks generally use a combination of wired and wireless links between computing devices, with wireless links usually used for the lowest level connections (e.g., end-node device to hub/gateway). In an example network, the edge wirelessly-connected) tier of the network is comprised of resource-constrained devices with specific functions. These devices may have a small-to-moderate amount of processing power and memory, and may be battery powered, thus requiring that they conserve energy by spending much of their time in sleep mode. A typical model is one where the edge devices generally form a single wireless network in which each end-node communicates directly with its parent node in a hub-and-spoke-style architecture (also known as a star network topology). The parent node may be, e.g., an access point on a gateway or a sub-coordinator which is, in turn, connected to the access point or another sub-coordinator.

Figure 1:
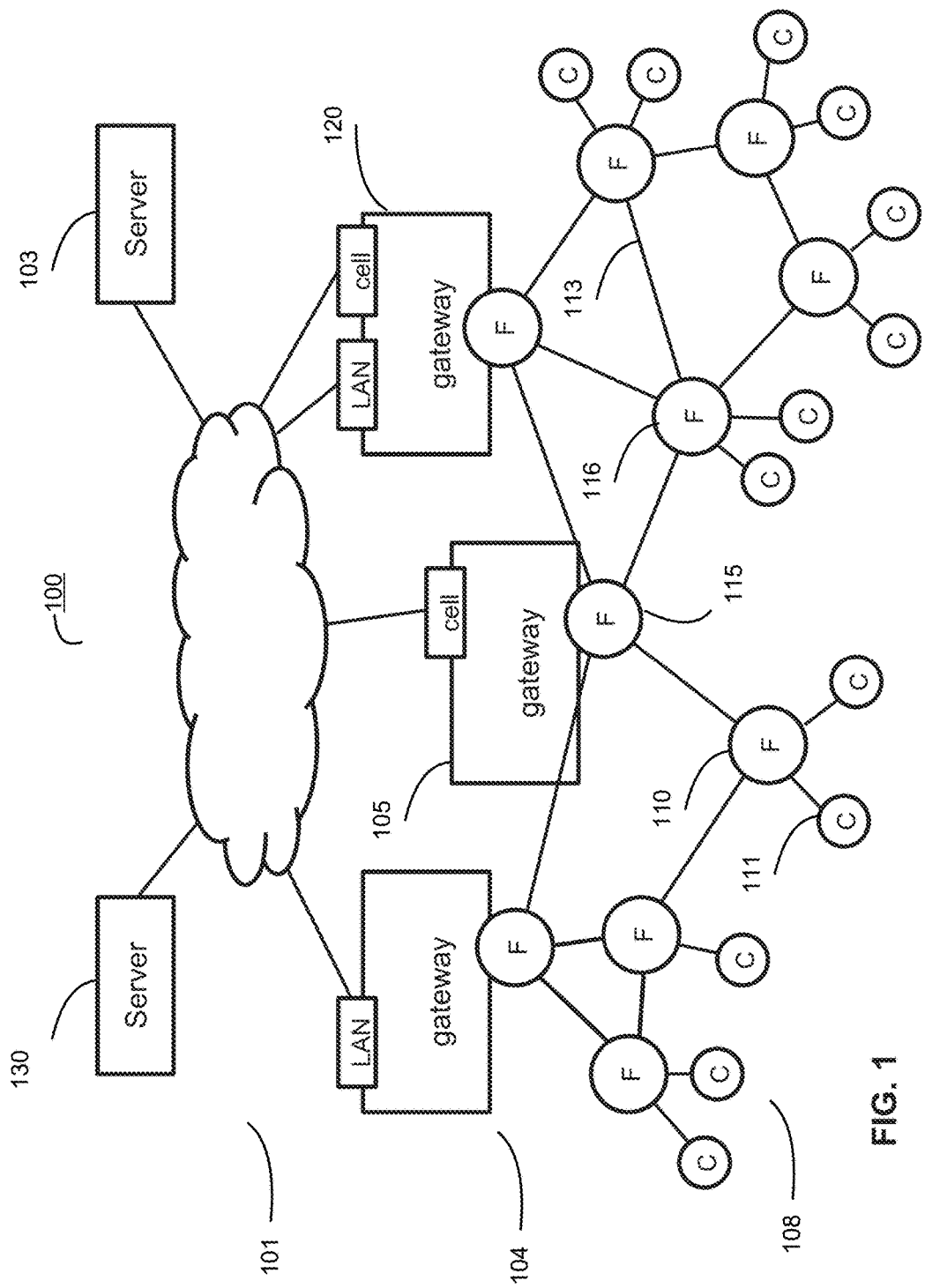
FIG. 1 is a schematic diagram of an example networked security system.

FIG. 1 shows an example (global) distributed network topology 100 for an example Wireless Sensor Network (WSN). In example network topology 100, upper tier 101 of the network may include traditional servers 103 and/or virtual servers running in a "cloud computing" environment and networked using appropriate networking technologies such as Internet connections. Applications running on those servers may communicate using XML/SOAP, RESTful web service, and/or other appropriate application layer technologies such as HTTP and ATOM.

In example network topology 100, middle tier 104 may include gateways 105 located at central, convenient places inside individual buildings and structures. Such gateways may communicate with the upper tier servers and cloud applications using web programming techniques or other appropriate technologies. These gateways 105 communicate with servers 103 in the upper tier whether the servers are stand-alone dedicated servers and/or cloud based servers running cloud applications using web programming techniques. The middle tier gateways 105 are also shown with both local area network (e.g., Ethernet or 802.11) and cellular network interfaces.

In example network topology 100, lower tier (edge layer) 108 may include fully-functional sensor nodes 110 (wireless devices, marked in FIG. 1 with "F") and constrained wireless sensor nodes or sensor end nodes 111 (marked in FIG. 1 with "C"). In some implementations, each gateway may be equipped with an access point (fully functional node or "F" node) physically attached thereto, which provides a wireless connection point to the other nodes in the wireless network.

Constrained computing devices as used herein are devices with substantially less persistent and volatile memory other computing devices, sensors in a detection system. Currently examples of constrained devices would be those with less than about a megabyte of flash/persistent memory, and less than 10-20 kilobytes (KB) of RAM/volatile memory). These constrained devices are configured in this manner; generally due to cost/physical configuration considerations.

In a typical network, the edge (wirelessly-connected) tier of the network is largely comprised of highly resource-constrained devices with specific functions, organized into sub-networks each of which is administered by a fully functional wireless node acting as sub-coordinator (i.e., coordinator of the sub-network). The end-node/constrained devices have a small-to-moderate amount of processing power and memory, and often are battery powered, thus requiring that they conserve energy by spending much of their time in sleep mode. A typical model is one where the edge devices generally form a single wireless network in which each end-node communicates directly with its parent node in a hub-and-spoke-style architecture. The parent node may be, e.g., an access point on a gateway or a sub-coordinator which is, in turn, connected to the access point or another sub-coordinator.

In example network topology 100, the communication links (illustrated by lines 113) shown in FIG. 1 are direct (single-hop network layer) connections between devices. A formal networking layer (that may function in each of the three tiers shown in FIG. 1) can use a series of these links, together with appropriate routing technology, to send messages (fragmented or unfragmented) from one device to another, over a physical distance. In other network topologies, each link may represent two or more hops and/or the configuration may be different than shown in FIG. 1.

In some example implementations, WSN state function based application layer uses an edge device operating system (not shown, but such as disclosed in the above mentioned provisional application) that allows for loading and execution of individual functions (after the booting of the device) without rebooting the device (so-called "dynamic programming"). In other implementations, edge devices could use other operating systems provided such systems allow for loading and execution of individual functions (after the booting of the device preferable without rebooting of the edge devices.

Example distributed network topology 100 may include or be part of a self-organizing network, such as a wireless mesh network. In some implementations, all of distributed network topology 100 is implemented using wireless mesh technology. In some implementations, only part of distributed network topology 100 is implemented using wireless mesh technology. For example, in FIG. 1, in some implementations, upper tier 101 may be implemented using standard network technology, and middle tier 104 and lower tier 108 may be implemented as one or more wireless mesh networks. In some implementations, upper tier 101 and middle tier 104 may be implemented using standard network technology, and tower tier 108 may be implemented using one or more wireless mesh networks. For example, a different wireless mesh network may be associated with each gateway, or a single wireless mesh network may include all of the gateways shown in FIG. 1 (and others), as well as all or some functional and sensor nodes.

In some implementations, wireless mesh network is a self-organizing wireless network, in which the network devices themselves establish communication links with one another. The communication links may be established by maintaining and updating routing tables associated with each network device. In the example implementations described herein, a wireless mesh network may be established between sensor, functional and/or gateway devices that are part of a larger building, or enterprise-wide system. In examples, such devices may be used for monitor and/or control in a security/intrusion, fire alarm, or other appropriate system. The devices report status information from their systems to a central monitoring service, which may include one or more host computing devices. For example, the central monitoring service may include server 103 and/or server 130, in addition to other computing equipment. The central monitoring service may also send control commands, which the devices use for configuration and/or control.

Figure 2:
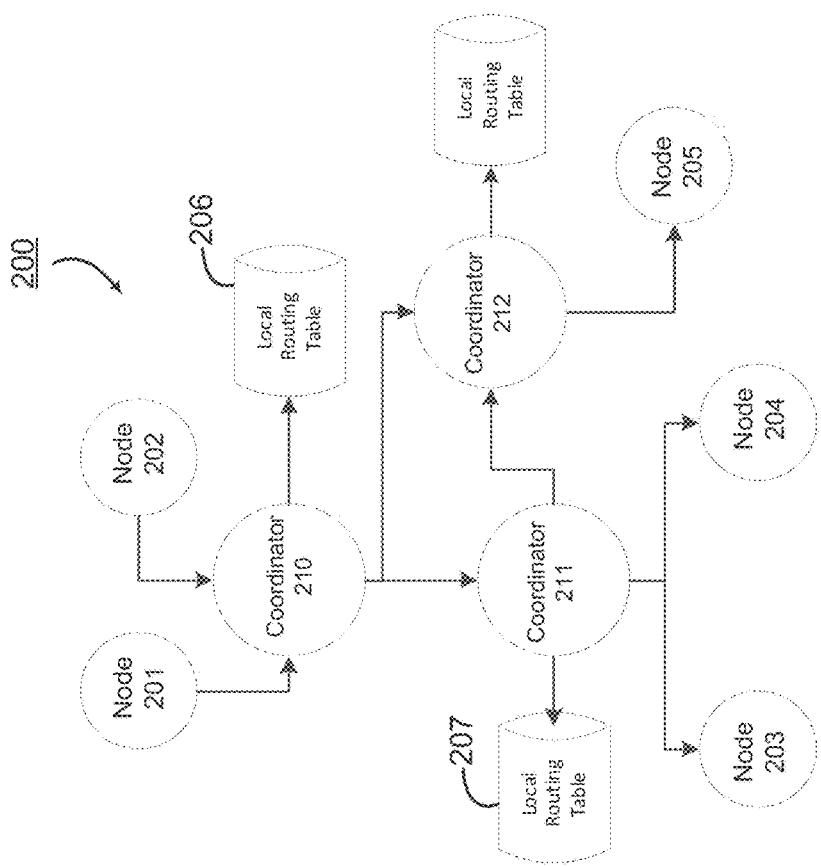
FIG. 2 is a block diagram of a portion of the networked security system of FIG. 1.

FIG. 2 shows components of an example wireless network 200 on which the processes described herein may be implemented. In the implementations described herein, wireless network 200 is a wireless mesh network, and may be part of the larger network shown in FIG. 1. However, in other implementations, the processes described herein may be performed using other types of networks.

Wireless network 200 may be a heterogeneous network, in which devices on wireless network 100 do not perform the same functions, or a homogeneous network, in which devices on wireless network 100 perform the same functions or substantially the same functions. Wireless network 100 includes nodes 201 to 205, which may, or may not, be endpoint devices on the network, such as sensors, monitors or the like. Typically, the primary connection between a node and the network is wireless; however, one or more of nodes 201 to 205 may also include a wired connection to network 200.

Wireless network 200 also includes coordinator devices 210 to 212, which may be intermediary devices on the network. In the example implementations described herein, a coordinator device, e.g., coordinator device 210, functions in its role in the networking layer as a router or repeater to forward data packets sent by a node, e.g., node 201 or node 204 (which need not be a directly connected node) or by another coordinator device, e.g., coordinator 211, along a path through wireless network 200. The coordinators 210-212 communicate with each other to maintain and update routing information to enable communication between devices, and to account for changes in the network 200. The coordinator devices store routing information, such as a next hop along a network path to a data packet's intended destination, and a hop on a return path. This information is stored in one or more local routing table(s) (e.g., local routing table 206, 207, 208) in memory on, or otherwise accessible to, the corresponding coordinator device. In some implementations, the nodes may also include one or more such routing table(s), particularly if the nodes are, or may become part of, a network pathway. The processes described herein may be used to build, and update, those routing tables, along with routing tables on any other appropriate network devices.

Nodes 201 to 205 and coordinator devices 210 to 212 may communicate via radio frequency (RF) links using any appropriate wireless protocol or protocols. Wireless network 200 may also include other types of devices (not shown), such as computers, base stations, or embedded processing devices that interact with the devices of FIG. 2.

Nodes 201 to 205 may each be either a source or a destination of network data. In some implementations, the nodes constitute, or are to, one or more sensors or controlling devices. The sensors are part, of physical systems, such as an alarm system or a security system, as noted above, and sense or monitor physical quantities, such as temperature, movement, or the like. Anode acquires analog and/or digital signals as a result of this sensing and transmit data packets corresponding to these signals to an appropriate device via wireless network 200. An antenna (not shown s included on each endpoint device to enable transmission. Antennas are also included on the other wireless devices in the network.

Multiple mesh networks may occupy the same physical space. Data packets for such networks may be differentiated, e.g., by a network group identifier (ID). Thus, the networks remain logically separate even though they occupy the same physical space.

Wireless mesh networks are typically established by one or more prospective network devices initiating communication to one or more other prospective network devices. For example, a first prospective network device (such as node 202) may output a packet identifying the first device (node 202) and in an attempt to locate other devices within the RF vicinity of the first device (node 202), with which the first device may connect. A second prospective network device (such as coordinator device 210) in that vicinity may respond and identify itself as a device that is available for connection to the first device. The two devices may then establish a connection through appropriate back-and-forth communications. This general process, or other(s) like it, may be repeated either by both devices or by other devices until the mesh network is formed. Typically, at least one of the devices is initially in communication with a base station or other wired connection to the central monitoring service, enabling connection between the wireless mesh network and the central monitoring service. Upon connection to the wireless network, routing tables throughout the wireless network may be updated.

Devices may enter, e.g., become part of, a wireless mesh network in the manner described above, or in any other appropriate manner. Likewise, devices may also leave the wireless mesh network. For example, devices may be deactivated or lose power, causing the devices to leave the network. In some cases, loss of a single device may affect communication to numerous other devices on the network. For example, a single device may be the primary pathway over which communications to numerous other devices pass. As a result, loss of that device also interrupts that primary path, necessitating re-routing of communications through the wireless mesh network. This re-routing can affect the contents of routing tables in nodes and coordinators.

The example processes described herein enable routing of data packets through a changing network environment resulting, e.g., from devices entering or leaving the network. This is done by updating configurable routing tables that are distributed across all or some routing nodes in the network. The processes may be used on wireless mesh networks of any size; however, they may have particular applicability to small-to medium-sized networks, in contrast to large wide area networks such as the Internet.

The implementation below is of wireless mesh network 200 updating routing tables based on packet transmissions through node 201 and coordinators 210, 211.

Figure 3:
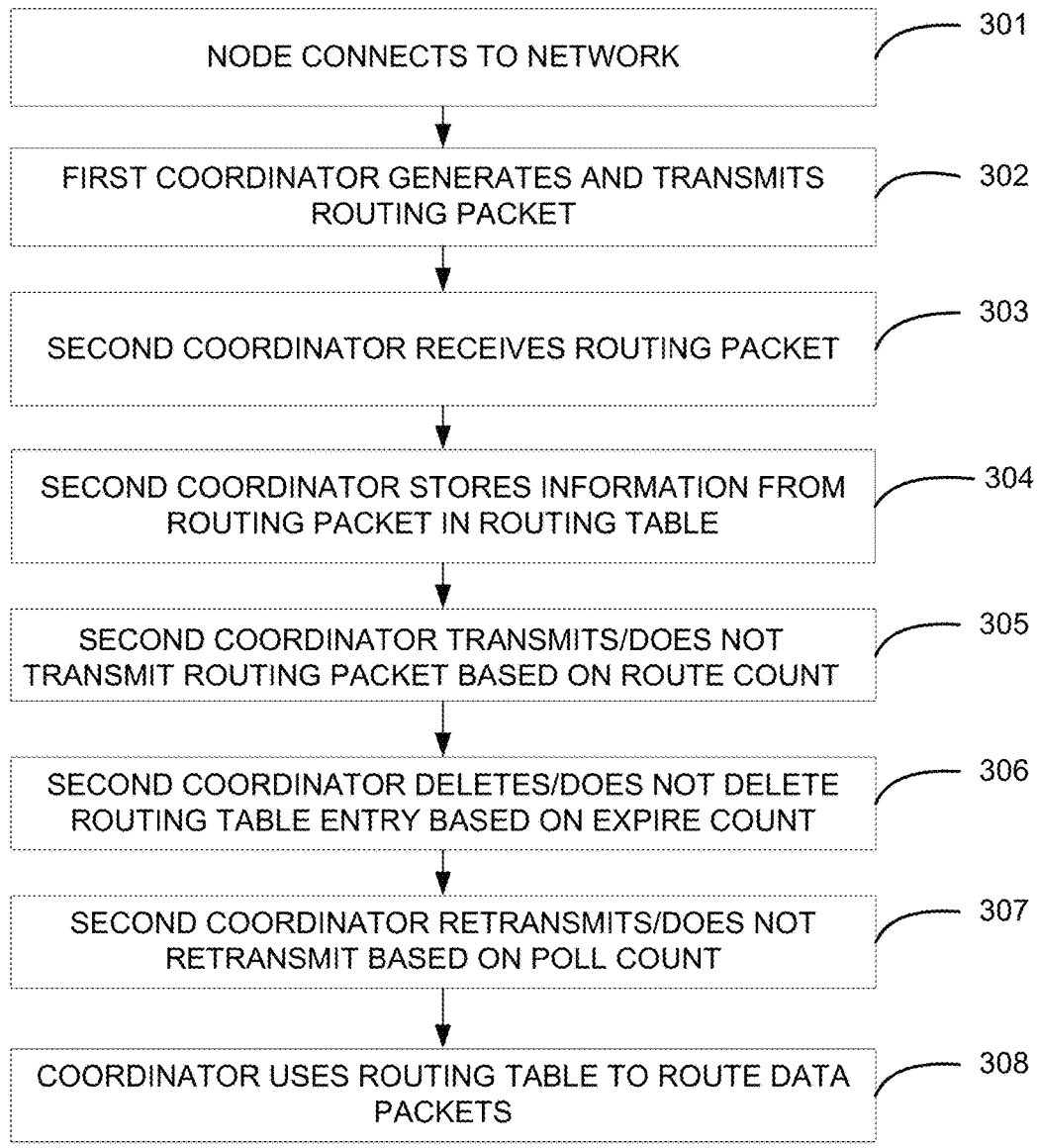
FIG. 3 is a flowchart showing an example process for maintaining routing tables in the network portion of FIG. 2.

Referring to the flowchart of FIG. 3, in this example implementation, a node (such as node 201) connects (301) to a network (such as network 200). Such connection may be implemented in any appropriate manner using one or more processes, e.g., through appropriate communication to coordinator 210. In response, a first coordinator (such as coordinator 210), to which the node has connected, generates and transmits (302) a routing packet containing, in its mesh header (the part of the packet reserved for routing information), the coordinator's short address, the node's short address, and an route count value of zero. In this example, the routing packet is transmitted to advise other devices (e.g., coordinators) in the RF vicinity of the first coordinator of the addition of the node to the network. Information in the routing packet is known to the first coordinator beforehand or is obtained through communication with the node. In this example implementation, a short address is a 2-byte/16-bit random, uniquely-assigned number that identifies a device (either a node, a coordinator, or another network device) within the network. In other implementations, the short address may be replaced by any other appropriate node and/or coordinator identification information. The route count is a value that is incremented at each node (hop), and is used as described below.

A second coordinator, such as coordinator 211, receives (303) the routing packet from coordinator 210. Coordinator 211 checks its routing table entries to determine if information from the routing packet is already present in the routing table. If that information is not already present (which it should not be at this point), coordinator 211 records (e.g., stores) (304), in its routing table 207, a routing entry that includes coordinator 210's short address, node 201's short address, and the route count incremented by one (the route count at coordinator 210 being set at zero). This routing entry is usable by coordinator 211 to route data to/from node 201.

Routing table 207 also stores an "expire count" and a "poll count" for each routing entry in routing table 207. The expire count is a value corresponding to (e.g., equal to) the greatest number of times a route entry will be checked before being deleted from the routing table. The poll count is a value corresponding to (e.g., equal to) the greatest number of times a routing table entry will be checked by a device before routing information for that entry is retransmitted. The values for the expire count and the poll count are either propagated through the network by the coordinators or are hard-coded into the routing table of each device. Other arrangements are possible. Each entry of the routing table may include counters corresponding to the expire count and to the poll count. These counters are incremented by one each time the corresponding routing table entry is checked. The corresponding counter values are compared to the expire count and poll count, and the results of the comparisons are used as described below.

Coordinator 211 performs a check to determine whether the route count incremented by one exceeds a maximum count stored in routing table 207. In this example implementation, the maximum count is a number corresponding to (e.g., equal to) the greatest number of hops through which a packet will be routed.

If the route count does not meet or exceed the maximum count, coordinator 211 transmits (305) the routing packet to other coordinators (such as coordinator 212) that are within its RF vicinity. Otherwise, if the route count meets or exceeds the maximum count, the routing packet is not transmitted. In this regard, if the route count meets or exceeds the maximum count, the maximum number of hops has been reached at coordinator 211. Thus, no further transmission of the routing packet is permitted, which is why the routing packet is not transmitted to another device (e.g., coordinator) on the network. The route count for each routing table entry may be stored in the routing table.

As coordinator 211 checks entries of its routing table 207, the corresponding expire counter and poll counters for entries in routing table 207 are each incremented by one, as described above. If an expire count value reaches the stored expire count, then the corresponding entry in the routing table is deleted (306). As noted, the expire count is a value corresponding to (e.g., equal to) the greatest number of times a route entry will be checked before being deleted from the routing table. Generally, the expire count is used to adjust the network's configuration resulting, e.g., from movement of nodes into or out of the network. If the expire count is reached, the corresponding routing entry is deleted on the assumption that the entry may no longer be valid. Notably, a check is not performed to determine whether the entry is still valid. Rather, the entry is assumed not to be valid any longer, and is deleted. Thus, the system forces the network to reestablish routing pathways after a certain number of checks (look-ups), thereby reducing the number of potentially invalid routes in the routing table.

If the poll count value reaches the stored poll count and the route count for a corresponding routing table entry has a value of zero (e.g., the device is the coordinator to generate the routing packet and thus the first coordinator to transmit the routing packet), then routing information for that entry is re-transmitted (307). This allows for periodic updating of routing table entries from source devices throughout the network.

A coordinator uses the routing table built and maintained in the manner described above to route data packets during normal network operation. For example, when a coordinator (e.g., coordinator 211) receives a regular (e.g., non-routing) data packet having the coordinator's short address in the mesh header, the coordinator uses the destination's short address (also found in the mesh header) to check for, and to identify corresponding values in the routing table, if available. The values may be, e.g., the address of one or more devices on a network path to the data packet's destination. In his example, coordinator 211 performs the check, and obtains the values from its routing table 207. The coordinator then uses the values obtained from its routing tables to re-address the mesh header of the packet to forward the packet to its destination. If the count is zero in the table, then the coordinator fills in the destination address in the mesh header instead of a coordinator address before sending the packet.

The nodes generally and coordinator nodes specifically may be implemented using any appropriate type of computing device, such as a mainframe work station, a personal computer, a server, a portable computing device, or any other type of intelligent device capable of executing instructions, connecting to a network, and forwarding data packets through the network. The nodes generally and coordinator nodes specifically can execute any appropriate computer programs to generate, receive, and transmit data packets for use on the network. Sensing and control nodes" or "end-nodes" are types of "nodes" as used herein. Some physical "nodes" in the network may simultaneously support both "coordinator functions" and "sensing and control functions." In some implementations a single physical device could house the functions of both a "sensing node" and a sub-coordinator.

Each of nodes 201 to 205 and coordinators 210 to 212 may include one or more non-transitory machine-readable media, such as computer memory (not shown), to store executable instructions. Each of these devices may also include one or more processing devices (e.g., microprocessors, programmable logic, application-specific integrated circuits, and so forth) for executing the instructions to perform all or part of the functions described herein. In some implementations, the structure of nodes 201 to 205 may be about the same as the structure of coordinators 210 to 212. This may not be the case in other implementations, e.g., their structures may be different. Each device, however, is programmable to implement appropriate functionality.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

An example, non-limiting application of the WSN of FIGS. 1 to 3 is in a security system for intrusion detection, fire, toxic gas, monitor, etc. installed at one or more premises such as one or more residential houses or building(s) and especially in, e.g., commercial, industrial, buildings, complexes, etc.

In some typical intrusion detection system implementations, an intrusion detection panel is included, whereas in others more sophisticated management systems are included. Sensors/detectors may be disbursed throughout the premises. The intrusion detection system may be in communication with a central monitoring station (also referred to as central monitoring center) via one or more data or communication networks (only one shown), such as the Internet; the phone system, or cellular communication system.

The intrusion detection panel may be configured to receive signals from plural detectors/sensors that send, to the intrusion detection panel, information about the status of the monitored premises. Several types of sensor/detectors (unless otherwise noted are used interchangeably herein) may be used. One type of detector is a detector that sends a binary signal that indicates presence or absence of an event. Examples of these types of detectors include glass break detectors and contact switches. Another type of detector sends metadata that includes information resulting from processing applied by the detector to inputs, e.g., raw data received by the sensor. Examples of these types of detectors may include microphones, motion detectors, smart switches and cameras, recognition devices and so forth.

Some of the detectors and sensors may be hard wired but in general the detectors communicate with systems wirelessly over the WSN. In general, detectors sense glass breakage, motion, gas leaks, fire, and/or breach of an entry point, and send the sensed information over the WSN, as needed and appropriate. Based on the information received from the detectors, the intrusion detection panel determines whether to trigger alarms, e.g., by triggering one or more sirens (not shown at the premise and/or sending alarm messages to the monitoring station.

As described above with respect to FIGS. 1 to 3, the WSN may include any combination of wired and wireless links that are capable of carrying packet and/or switched traffic, may span multiple carriers and a wide geography, and hay have the features discussed above. In an example implementation, portions of WSN may include the Internet. In another implementation, the WSN may include one or more wireless links, and may include a wireless data network, e.g., with tower such as a 2G, 3G, 4G or LYE cellular data network. The panel may be in communication with the network by way of Ethernet switch or router (not illustrated). The panel may include an Ethernet or similar interface, which may be wired or wireless. Further network components, such as access points, routers, switches, DSL modems, and the like possibly interconnecting the panel with the data network are not illustrated.

The functionality of one or more gateways and/or others of the network devices described above may be distributed among various devices, as described below.

In this regard, in a networking context, the term "cloud" may include a variety of services and applications that reside outside of hardware that is managed or controlled by a user. There are several scenarios that illustrate this concept, such as a website where users access web applications, or an online library where a database resides in a centralized or distributed external location rather than on the user's computers. The traditional architecture for this paradigm is usually a user interface (UI), where the external users connect, via an application program interface (API), to some type of database to manage the information. The user interface submits requests via an API to a cloud server. Typically, each of these requests is processed by modular programs called "agents" or "workers" that run on the cloud-based server, and not in the users' computer. These agents may execute tasks assigned by the users, for example, to query the database or to execute a complex operation involving data and user input.

A new paradigm in device connectivity has been emerging during the past several years. For example, microprocessors embedded in devices are increasingly becoming connected to the Internet so that they can individually provide data about device performance or operating characteristics to remove locations. Many of these devices, such as temperature controllers, smoke detectors, or lighting control switches residing in buildings can be connected wirelessly to a building network, called a wireless sensor network (e.g., a wireless mesh network), and to an external network via a data aggregation and monitoring device called a gateway. In some examples, the gateway collects and aggregates data so that it can be forwarded to the cloud.

The devices, such as temperature controllers, smoke detectors, or lighting control switches, are, or are connected to, end nodes, which may be devices that read sensor data and that connect to a gateway via the sensor network using one or more message routing hops. The gateway aggregates data from these end nodes, and sends that data to the "cloud" server. The cloud may include an external server or cluster of servers that saves the information and is able to respond to user requests. The cloud may also have rules, workers and agents looking (e.g., monitoring) for a particular condition to trigger a specific action.

If the gateway loses communication with the "cloud" server, the functionality of the system may degrade to the point where the nodes become isolated. Each gateway may continue to save sensor data locally until the local memory is full. The capabilities of the system may be reduced by this isolation and the data by itself will not execute action. For example, a door will not be opened in the case of fire because the rules and the decisions are made in the cloud.

Thus, a building could contain dozens of gateways and thousands of end node devices, but with no connection to the cloud, so no action is going to occur. One of the reasons for this situation is the complexity and the scalability of the architecture. Accordingly, described herein is an example of a local architecture that provides the scalability and replication that exists in a typical cloud architecture, but which is deployable on a more resource-constrained system of the gateway and local sensor network. Consequently, in some implementations, the scalability of the cloud system can be duplicated and extended so that the scalability of cloud architecture can be replicated locally at the site location. The databases, the rule engines, the workers, the agents, and queues that are found in a typical cloud architecture require can also be implemented locally (e.g., in the sensor network) using the distributed architecture described herein. Because the processes and distributed architectures have the ability to scale, relatively simple devices like gateways can contain all of (or at least a subset of) the capabilities that exist in the "cloud". As a result, in some cases, the functionality of the "cloud" can continue to operate locally in one or more gateways, despite the absence of connection to an external cloud.

As noted above, in this example, the distributed architecture is scalable, meaning it can be deployed in one device or in thousands of devices in a network. In some examples, the distributed architecture allows the adding of nodes to a cluster and includes no single point of failure. In this example, a cluster includes multiple devices, which may be configured (e.g., programmed) to cooperate to implement a particular functionality.

In some implementations, there is no need for connection to external cloud or, in the case a connectivity failure to the cloud, the example processes described herein allow the gateway or set of gateways to log information amongst themselves, e.g., in one or more distributed local databases. This allows one or more gateways to make decisions using a rule engine that is distributed among the gateways. A feature of this example distributed architecture is that the cloud functionality continues to operate locally among the gateways as long as a single gateway continues to run. In some implementations, this is because of the distribution of the distributed architecture and because the distributed architecture has redundant functionality and, thus, no single point of failure.

Figure 4:
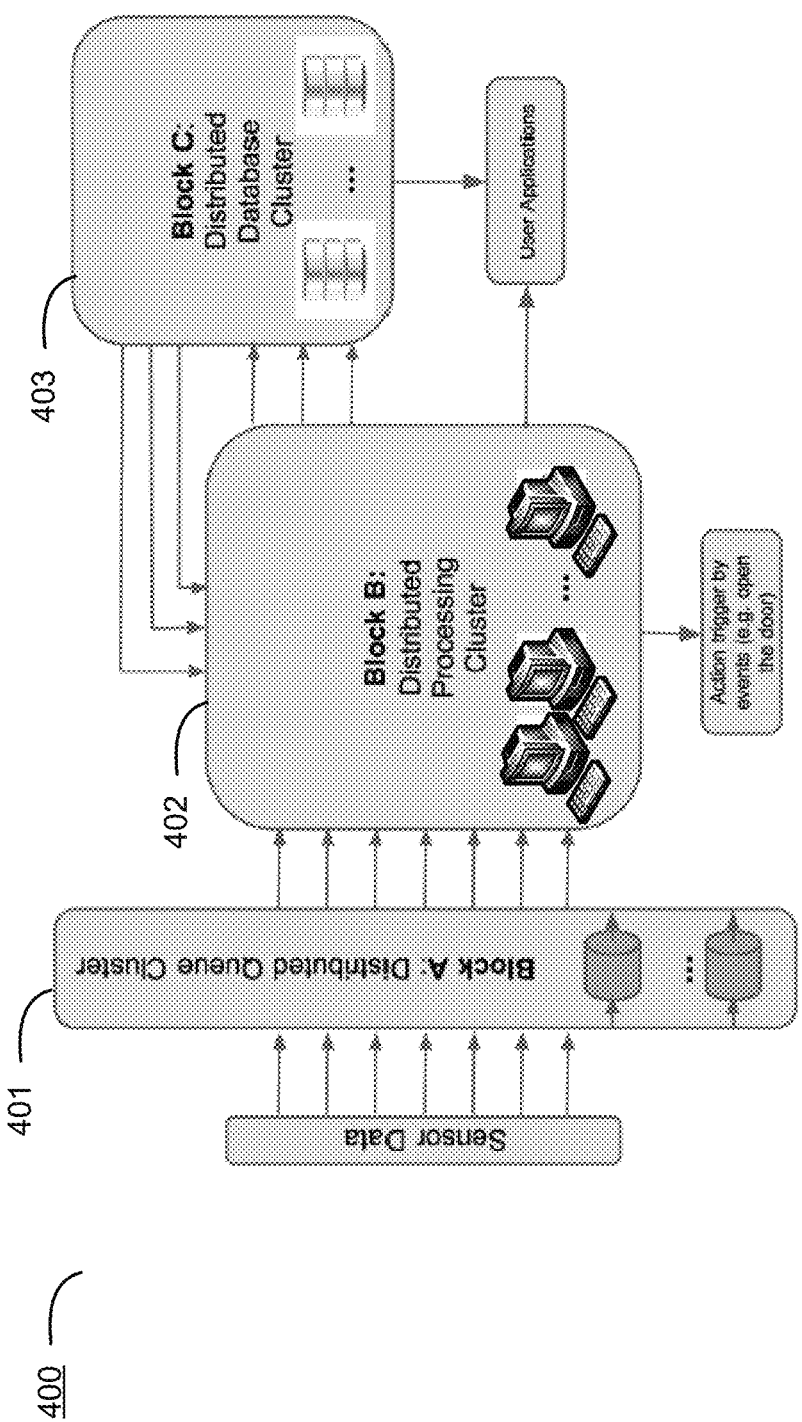
FIG. 4 is a block diagram of an example distributed processing system for use in a sensor network.

FIG. 4 shows a diagram of an example implementation of the distributed architecture 400 described herein. The first block (Block A) 401 of the diagram represents a distributed queue cluster (system). In this example, the queue cluster comprises multiple network devices that cooperate to communicate with end nodes of a network (e.g., node 111 of FIG. 1) and to store information from the end nodes in memory (e.g., one or more hardware storage devices). In operation, communication, represented by messages, comes from sensor data captured at end nodes of the sensor (e.g., wireless mesh) network. The communications are stored in one or more devices in the queue cluster. In this example, every node within the queue cluster presents a RESTful API to the outside world. A purpose of the RESTful API is to decouple, and to allow, any user to communicate with the system in a well-defined interface, avoiding, for instance, a requirement that the user or end device have knowledge the native language of the queue cluster. This cluster or any cluster includes appropriate communication channels between the nodes of the clusters.

The second block on FIG. 4 (Block B) 402 represents an example distributed parallel processing cluster (system). In this example, the processing cluster comprises multiple network devices that cooperate to perform one or more operations on the information from the queue cluster. In this example, this system does not present a single point of failure and all the nodes play the same, or a similar, role. In this example, there are no master or slave nodes. However, in some implementations, there is a leader node that is chosen for one or more tasks (e.g., every task) executed in the processing cluster. The leader node is primarily responsible for execution of the given task, whether it be execution by the leader node itself or coordination of execution among one or more other nodes. When the leader fails, the other nodes agree upon the selection of the new leader for a particular task. This distributed parallel system receives a task or assignation, and can execute a limited task or an unlimited task or until a particular condition occur.

A worker (not shown), which in this example includes a set of rules to act on the data received, may be distributed across the nodes within the cluster according to a replication factor or on demand. When the processing cluster 402 determines that a worker is over-loaded, in this implementation the processing cluster 402 automatically launches more instances of the worker within the cluster of local nodes. In some implementations, the upper limit (e.g., the maximum number of instances) is defined in configuration parameters at the moment when submitting or commissioning a worker to the cluster. In some implementations, there is no upper limit, except as defined by limits of the hardware. The worker can take data from a queue cluster, from other workers, or from a database. The worker stores the result of its processing in a queue cluster, under a given topic, and registers the result in the database cluster or passes the result to another worker The third block (Block C) 403 represents an example distributed database cluster (system) having no single point of failure. The database cluster 403 comprises multiple network devices that cooperate to provide storage for use by the processing cluster. For example, processed data can be stored in the database cluster, data can be retrieved from the database cluster for processing, and so forth. In this example implementation, every node in the data cluster plays the same role in the cluster (no masters no slaves); the database data model is a key-value pair; and a unique key contains a set of values related to the key. In this example, the database also contains a support replication factor per record (value pair, within a key), and a support consistency level per record for writes and reads. In this example, this database exposes a RESTful API and also a native interface when speed is a concern.

The three cluster approach described above forms an example basic distributed architecture 400. In the example implementations described herein, the separation of roles occurs at the function level, rather than at the server level. Accordingly, in the example implementations described herein, every node of the network can become a node of the queue, a node of the processing cluster, or a node of the database cluster at any time and/or at the same time. A physical server can perform the three roles at the same time, which may result in full scalability, from one physical server to hundreds or thousands of servers.

Figure 5:
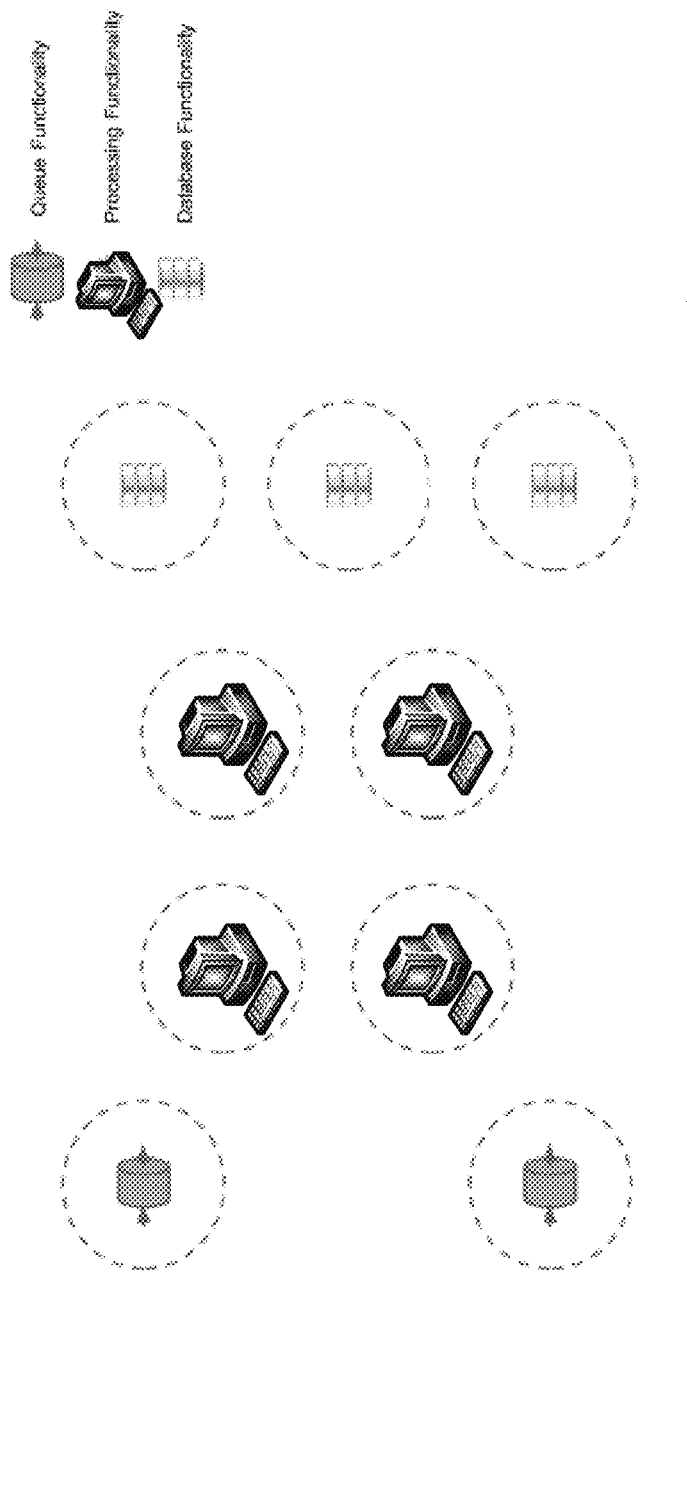
FIG. 5 is a conceptual diagram of a physical server showing different roles (queue, processing, and database) that the physical server performs in the distributed processing system.
Figure 6:
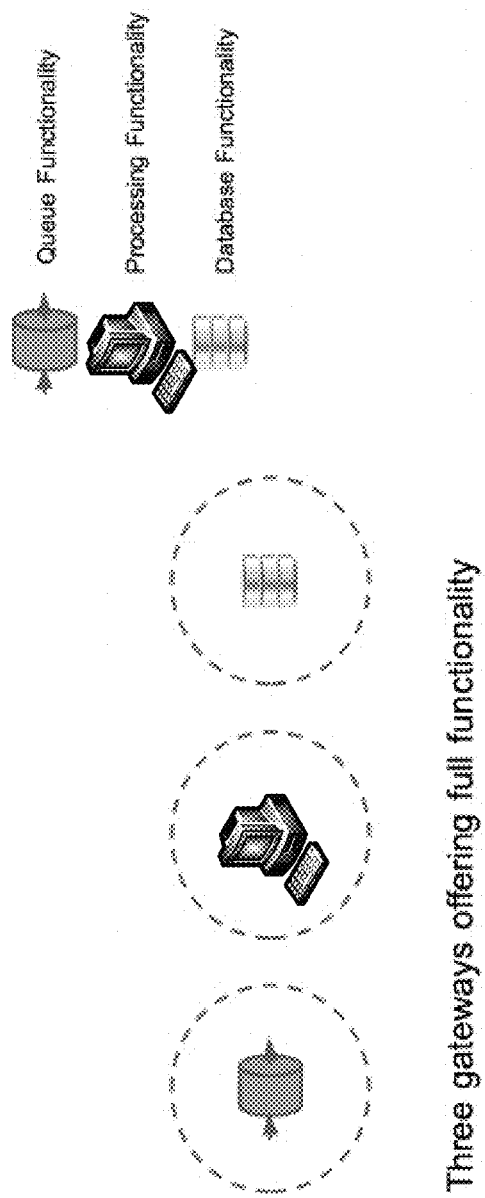
FIG. 6 is a conceptual diagram showing physical servers performing different, single roles in the distributed processing system.
Figure 7:
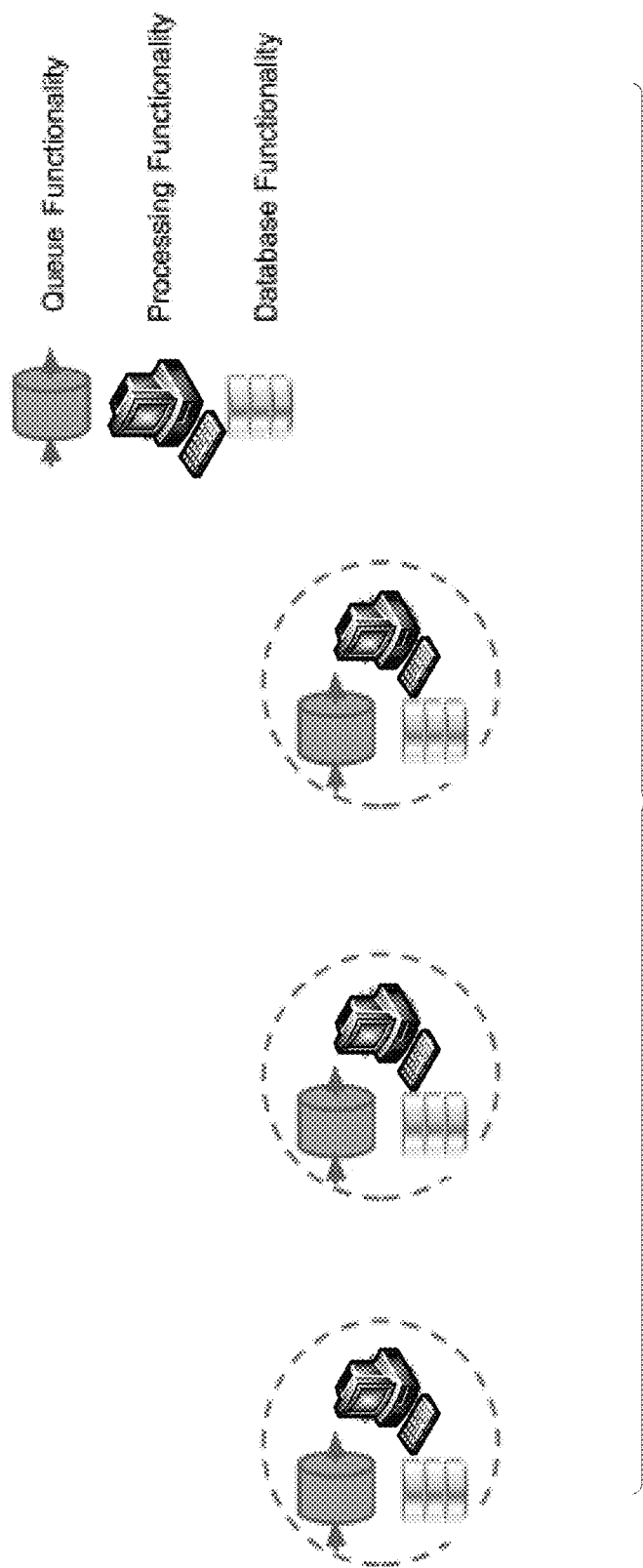
FIG. 7 is a conceptual diagram showing different physical servers each performing multiple different roles in the distributed processing system.

FIGS. 5-7 show, conceptually, different roles (queue, processing, and database) that different physical servers, including gateways that are implemented as servers or other computing devices, may perform at different times. FIG. 5 shows an implementation where a single gateway (e.g., gateway 105 of FIG. 1) is configured to perform the three roles at the same time. The capacity of the gateway may be limited by the processing power of its CPU and a memory capacity of the queue cluster and the database.

FIG. 6 shows an implementation where several gateways are used, and the clusters are defined based on the roles that they perform. For instance, in an example having three gateways, each gateway assumes a different role: one gateway operates as a database, another operates as a queue, and another operates as a processor.

FIG. 7, shows another example implementation, where three gateways operate as a database, a queue, and a processor at the same time. In this example implementation, the failure of one gateway will likely not cause damage to the system since, in this example, two remaining gateways (or even one remaining gateway) can support the system.

In these example implementations, since internal gateways offer cloud services, the connection to an external network ("the cloud") will typically not constitute a point of failure.

Although the processes presented herein are described in the context of communications within a wireless mesh network and to/from an external network such as the Internet, the processes may be used in any appropriate network.

In the example implementations described herein, the queue cluster (Block A of FIG. 4), the distributed processing cluster (Block B of FIG. 4) and, the distributed database cluster (Block C of FIG. 4) may include multiple devices on the network (e.g., nodes, gateways, servers or the like) Each of these network devices may include one or more processing devices (e.g., microprocessors, programmable logic, application-specific integrated circuits, and so forth) for executing the instructions to perform all or part of their corresponding functions described herein. In some implementations, the structure of different devices may be the same or about the same, or the structures of different devices may be different. Each device, however, is programmed with appropriate functionality.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

In example implementations, each of the network devices described herein (e.g., including, but not limited to, a server, a gateway, coordinators/sub-coordinators, and end-nodes) may include one or more non-transitory machine-readable media, such as computer memory (not shown), to store executable instructions. Each of the network devices may also include one or more processing devices (e.g., microprocessors, programmable logic, application-specific integrated circuits, and so forth) for executing the instructions to perform all or part of their corresponding functions described herein. In some implementations, the structure of different devices may be the same or about the same, or the structures of different devices may be different. Each device, however, is programmed with appropriate functionality.

Figure 8:
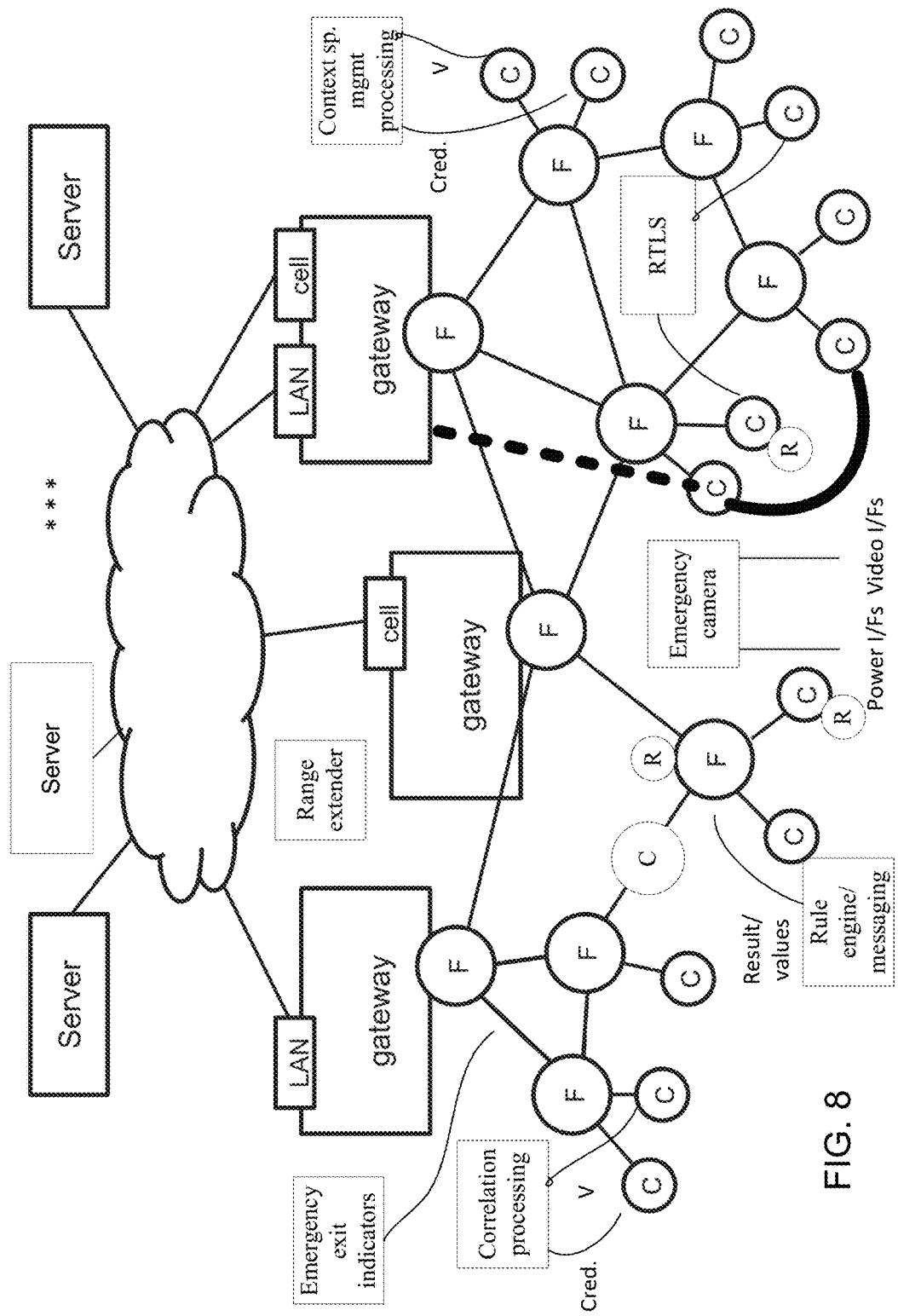
FIG. 8 is a block diagram of components of an example networked security system.

FIG. 8 shows an example of a security system having features of the WSN described with respect to FIGS. 1 to 7 and having the various functionalities described herein. As shown in FIG. 8, correlation processing receives inputs from certain constrained nodes (although these can also be fully functional nodes). These inputs may include credential information and video information, and the correlation processing may produce correlated results that are sent over the network. Context management processing receives inputs from certain constrained nodes (although these can also be fully functional nodes) e.g., credential information and video and grouping information, and performs context processing with results sent over the network. The network supports operation of emergency exit indicators; emergency cameras as well as distributed rule processing and rule engine/messaging processing. Range extenders are used with e.g., gateways, and a real time location system receives inputs from various sensors (e.g., constrained type) as shown. Servers interface to the WSN via a cloud computing configuration and parts of some networks can be run as sub-nets.

The sensors provide in addition to an indication that something is detected in an area within the range of the sensors, detailed additional information that can be used to evaluate what that indication may be without the intrusion detection panel being required to perform extensive analysis of inputs to the particular sensor.

For example, a motion detector could be configured to analyze the heat signature of a warm body moving in a room to determine if the body is that of a human or a pet. Results of that analysis would be a message or data that conveys information about the body detected. Various sensors thus are used to sense sound, motion, vibration, pressure, heat, images, and so forth, in an appropriate combination to detect a true or verified alarm condition at the intrusion detection panel.

Recognition software can be used to discriminate between objects that are a human and objects that are an animal; further facial recognition software can be built into video cameras and used to verify that the perimeter intrusion was the result of a recognized, authorized individual. Such video cameras would comprise a processor and memory and the recognition software to process inputs (captured images) by the camera and produce the metadata to convey information regarding recognition or lack of recognition of an individual captured by the video camera. The processing could also alternatively or in addition include information regarding characteristic of the individual in the area captured/monitored by the video camera. Thus, depending on the circumstances, the information would be either metadata received from enhanced motion detectors and video cameras that performed enhanced analysis on inputs to the sensor that gives characteristics of the perimeter intrusion or a metadata resulting from very complex processing that seeks to establish recognition of the object.

Sensor devices can integrate multiple sensors to generate more complex outputs so that the intrusion detection panel can utilize its processing capabilities to execute algorithms that analyze the environment by building virtual images or signatures of the environment to make an intelligent decision about the validity of a breach.

Memory stores program instructions and data used by the processor of the intrusion detection panel. The memory may be a suitable combination of random access memory, and read-only memory, and may host suitable program instructions (e.g. firmware or operating software), and configuration and operating data and may be organized as a file system or otherwise. The stored program instruction may include one or more authentication processes for authenticating one or more users. The program instructions stored in the memory of the panel may further store software components allowing network communications and establishment of connections to the data network. The software components may, for example, include an internet protocol (IP) stack, as well as driver components for the various interfaces, including the interfaces and the keypad. Other software components suitable for establishing a connection and communicating across network will be apparent to those of ordinary skill.

Program instructions stored in the memory, along with configuration data may control overall operation of the panel.

The monitoring server includes one or more processing devices (e.g., microprocessors), network interface and a memory (all not illustrated). The monitoring server may physically take the form of a rack mounted card and may be in communication with one or more operator terminals (not shown). An example monitoring server is a SURGARD™ SG-System III Virtual, or similar system.

The processor of each monitoring server acts as a controller for each monitoring server, and is in communication with, and controls overall operation, of each server. The processor may include, or be in communication with, the memory that stores processor executable instructions controlling the overall operation of the monitoring server. Suitable software enable each monitoring server to receive alarms and cause appropriate actions to occur. Software may include a suitable Internet protocol (IP) stack and applications/clients.

Each monitoring server of the central monitoring station may be associated with an IP address and port(s) by which it communicates with the control panels and/or the user devices to handle alarm events, etc. The monitoring server address may be static, and thus always identify a particular one of monitoring server to the intrusion detection panels. Alternatively, dynamic addresses could be used, and associated with static domain names, resolved through a domain name service.

The network interface card interfaces with the network to receive incoming signals, and may for example take the form of an Ethernet network interface card (NIC). The servers may be computers, thin-clients, or the like, to which received data representative of an alarm event is passed for handling by human operators. The monitoring station may further include, or have access to, a subscriber database that includes a database under control of a database engine. The database may contain entries corresponding to the various subscriber devices/processes to panels like the panel that are serviced by the monitoring station.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Tangible, physical hardware storage devices that are suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

In addition, the logic flows depicted in the figures do not require the particular order shown, or, sequential order, to achieve desirable results. In addition, other actions may be provided, or actions may be eliminated, from the described flows, and other components may be added to, or removed from, the described systems. Likewise, actions depicted in the figures may be performed by different entities or consolidated.

Elements of different embodiments described herein may be combined to form other embodiments not specifically set forth above. Elements may be left out of the processes, computer programs, Web pages, etc. described herein without adversely affecting their operation. Furthermore, various separate elements may be combined into one or more individual elements to perform the functions described herein.

Other implementations not specifically described herein are also within the scope of the following claims.

What is claimed is:

1. A system comprising:
 a distributed queue cluster comprising a plurality of first device nodes that cooperate to:
  receive messages comprising information from sensor devices over a wireless mesh network;
  store the information in local memory of at least one of the first device nodes; and
  wherein each of the plurality of first device nodes presents a RESTful API;
 a distributed processing cluster comprising a plurality of second device nodes that cooperate to:
  retrieve the information stored in the distributed queue cluster;
  select a device node among the second device nodes as a leader, wherein the leader launches one or more worker routines distributed across the plurality of second device nodes, wherein the one or more worker routines comprise one or more rules to act on the information to produce processing results; and
  wherein the leader launches one or more additional worker routines in response to determining a worker is over-loaded;
 a distributed database cluster comprising a plurality of third device nodes that cooperate to store in local memory the processing results produced from the distributed processing cluster; and
 wherein the distributed queue cluster, the distributed processing cluster, and the distributed database cluster are configured to connect to the wireless mesh network, the wireless mesh network configurable to connect to an external network, and with each of the first, second and third device nodes are configurable by assigning functional roles as either a node of the distributed queue cluster or a node of the distributed processing cluster or a node of the distributed database cluster.

2. The system of claim 1, wherein the distributed queue cluster of first device nodes, the distributed processing cluster of second device nodes, and the distributed database cluster of third device nodes are further configurable to comprise at least some devices in common.

3. The system of claim 1, wherein at least some of the functions of the first, second and third device nodes are redundant in each of the distributed queue cluster, the distributed processing cluster, and the distributed database cluster.

4. The system of claim 1, wherein the leader is a first leader and the distributed processing cluster is configured to select a second leader in response to an event associated with the first leader.

5. The system of claim 4, wherein the event comprises failure of the first leader.

6. The system of claim 1, wherein the one or more worker routines are configured to share the processing results.

7. The system of claim 1, wherein the distributed processing cluster is configured to define a maximum number of worker routines.

8. A computer program product tangibly stored on one or more computer-readable hardware storage devices, the computer program product comprising instructions executable by a processor to:
 cause first local device nodes to cooperate to form a queue cluster to communicate via a RESTful API with sensor end nodes (end nodes) of a wireless mesh network, receive information from the end nodes of the wireless mesh network, store the information from the end nodes in memory;
 cause second local device nodes to cooperate to:
  form a processing cluster to retrieve the information stored in the queue cluster;
  select an end node as a leader, wherein the leader launches one or more worker routines distributed across the second local device nodes, wherein the one or more worker routines comprises one or more rules to act on the information to produce results; and
  wherein the leader launches one or more additional worker routines in response to determining a worker routine is over-loaded;
 cause third local device nodes to cooperate to:
  form a database cluster to provide storage for the results produced from the processing cluster; and wherein the first, the second, and the third local device nodes configured to connect to the wireless mesh network, and the wireless mesh network configurable to connect to an external network, and with each of the first, the second, and the third local device nodes configurable to be assigned functional roles as either a node of the queue cluster or a node of the processing cluster or a node of the database cluster.

9. The computer program product of claim 8, wherein the queue cluster of first local device nodes, the processing cluster of second local device nodes, and the database cluster of third local device nodes all comprise at least some devices in common.

10. The computer program product of claim 8, wherein at least some of the functions of the first, second and third local device nodes are redundant in each of the queue cluster, the processing cluster, and the database cluster.

11. The computer program product of claim 8, wherein the leader is a first leader and the processing cluster is configured to select a second leader in response to an event associated with the first leader.

12. The computer program product of claim 11, wherein the event comprises failure of the first leader.

13. The computer program product of claim 8, wherein the one or more worker routines are configured to share the processing results.

14. The computer program product of claim 8, wherein the processing cluster is configured to define a maximum number of worker routines.

15. A method, comprising:
configuring local nodes as first local device nodes to form a distributed queue cluster, second local device nodes to form a processing cluster, and third local device nodes to form a database cluster, with any of the first, second and third local device nodes configurable to be assigned functional roles as either a node of the distributed queue cluster or a node of the processing cluster or a node of the database cluster;
receiving information from sensor end nodes (end nodes) over a wireless mesh network by the distributed queue cluster, the distributed queue cluster communicating with the end nodes using a RESTful API, which stores the information from the end nodes in memory;
performing one or more tasks on the information from the distributed queue cluster by the processing cluster that selects a node among the second local device nodes as a leader, wherein the leader retrieves information stored in the distributed queue cluster and launches one or more worker routines to process the information to produce processing results;
storing the processing results from the processing cluster in the database cluster; and
wherein the leader launches one or more additional worker routines in response to determining a worker is over-loaded; and
connecting the first local device nodes, the second local device nodes, and the third local device nodes to the wireless mesh network and the wireless mesh network configurable to connect to an external network.

16. The system of claim 6, wherein sharing the processing results comprises at least one of storing the processing results in the distributed queue cluster, storing the processing results in the distributed database cluster, or passing the results to a different worker routine of the one or more worker routines.

17. The system of claim 13, wherein sharing the processing results comprises at least one of storing the processing results in the queue cluster, storing the processing results in the database cluster, or passing the results to a different worker routine of the one or more worker routines.

18. The method of claim 15, wherein the distributed queue cluster of the first local device nodes, the processing cluster of the second local device nodes, and the database cluster of the third local device nodes are further configurable to comprise at least some nodes in common.

19. The method of claim 15, wherein the leader is a first leader and the processing cluster is configured to select a second leader in response to an event associated with the first leader.

20. The method of claim 19, wherein the event comprises a failure of the first leader.

* * * * *